United States Patent

Farris et al.

[11] Patent Number: 5,154,695
[45] Date of Patent: Oct. 13, 1992

[54] FOOT SPLINT

[75] Inventors: Harold J. Farris, Seminole; J. Marvin Winn, Largo; Joseph P. Morrissey, Seminole, all of Fla.

[73] Assignee: L'Nard Associates, Inc., St. Petersburg, Fla.

[21] Appl. No.: 621,598

[22] Filed: Nov. 27, 1990

Related U.S. Application Data

[63] Continuation of Ser. No. 247,104, Sep. 20, 1988, Pat. No. Des. 317,651.

[51] Int. Cl.⁵ .............................. A61F 3/00
[52] U.S. Cl. ........................... 602/27; 128/892
[58] Field of Search ............. 128/80 R, 80 H, 82.1, 128/77, 80 C, DIG. 15, 171, 892, 893, 68.1, 53-62, 882; 602/27, 28, 29

[56] References Cited

U.S. PATENT DOCUMENTS

| | | | |
|---|---|---|---|
| 3,606,884 | 9/1971 | Peter | 128/892 |
| 3,976,059 | 8/1976 | Lonardo | 128/80 |
| 4,076,022 | 2/1978 | Walker | 128/82.1 |
| 4,197,845 | 4/1980 | Browning | 128/892 |
| 4,263,905 | 4/1981 | Couch | 128/892 |
| 4,320,748 | 3/1982 | Racette | 128/D15 |
| 4,693,239 | 9/1987 | Clover | 128/80 |
| 5,020,523 | 6/1991 | Bodine | 602/27 |

*Primary Examiner*—Robert A. Hafer
*Assistant Examiner*—David J. Kenealy
*Attorney, Agent, or Firm*—Zarley, McKee, Thomte, Voorhees & Sease

[57] ABSTRACT

This invention pertains to a plastic foot splint having a horizontal foot portion, a contoured upstanding leg portion and a heel portion connecting the foot and leg portions. The heel portion has a rearward side portion with an aperture therein to permit visual examination of the rearward portion of a patient's heel when the foot splint is mounted on one of the patient's feet. A stabilizer bar is pivotally secured by one of its ends to the leg portion. Ratchet teeth are located on one end of the stabilizer bar and on the leg portion at the location of its pivotal connection to the stabilizer bar to permit the stabilizer bar to be selectively held in a fixed position with respect to the leg portion.

6 Claims, 2 Drawing Sheets

FOOT SPLINT

This application is a continuation of co-pending application Ser. No. 07/247,104 filed Sep. 20, 1988, and is now U.S. Pat. No. D317,651.

BACKGROUND OF THE INVENTION

Therapeutic leg and foot splints are commonly used on bedfast patients to correct or facilitate the healing of a variety of problems relating to the patient's feet. The functional aspects of such splints are disclosed and fully discussed in U.S. Pat. No. 3,976,059 issued Aug. 24, 1976. The splint of that patent discloses a curved heel portion that is enlarged with respect to a patient's foot to permit lateral visible examination of the patient's heel. That patent also discloses a stabilizer bar which can extend laterally from the back of the splint to hold the splint, and hence the patient's foot or leg, in a predetermined desirable position.

However, since the sores on a bedfast patient's heel are commonly on the rearward surface of the heel, the splint of said patent does not permit full visibility of the patient's heel. Furthermore, the stabilizer bar of this patent does not have sufficient interlocking surfaces with the splint to always prevent the stabilizer bar from becoming disaligned from its desired predetermined position.

Therefore, it is a principal object of this invention to provide a plastic foot splint which has an aperture in the rearward portion of the heel to permit visual examination of the rearward portion of a patient's heel who is wearing the splint. Visibility is gained through the aperture of this invention, depending on the position of the patient, either by direct visual contact, or by the use of a mirror held in spaced relation to the aperture.

A further object of this invention is to provide interlocking ratchet teeth between one end of the stabilizer bar and the rearward surface of the leg portion of the splint to insure that the stabilizer bar will not be inadvertently moved from its desired position by the weight of the patient's leg or movement of the patient's leg.

These and other objects will be apparent to those skilled in the art.

BRIEF SUMMARY OF THE INVENTION

This invention pertains to a plastic foot splint having a horizontal foot portion, a contoured upstanding leg portion and a heel portion connecting the foot and leg portions. The heel portion has a rearward side portion with an aperture therein to permit visual examination of the rearward portion of a patient's heel when the foot splint is mounted on one of the patient's feet.

A stabilizer bar is pivotally secured by one of its ends to the leg portion. Ratchet teeth are located on one end of the stabilizer bar and on the leg portion at the location of its pivotal connection to the stabilizer bar to permit the stabilizer bar to be selectively held in a fixed position with respect to the leg portion.

DESCRIPTION OF THE PREFERRED EMBODIMENT

Figure 1:
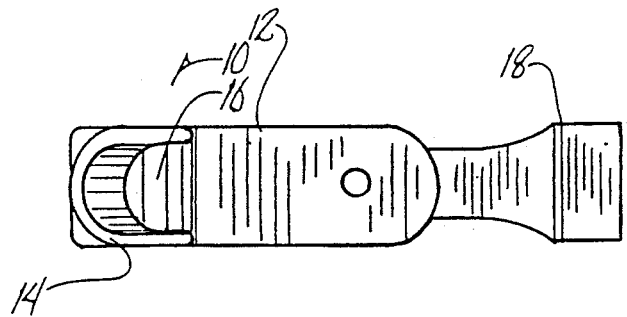
FIG. 1 is a top plan view of the foot splint of this invention.
Figure 2:
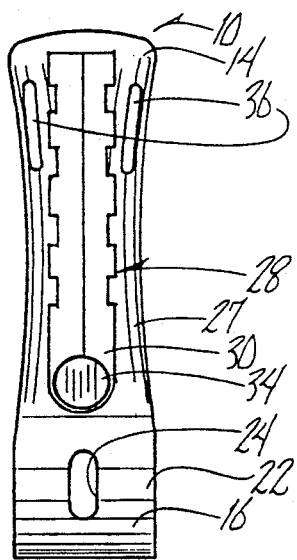
FIG. 2 is a rear elevational view thereof.

Foot splint 10 is comprised of a generally horizontal foot portion 12, a substantially vertical leg portion 14, both of which are interconnected by a curved heel portion 16. The splint is preferably comprised of a resilient plastic material and is preferably of integral construction. The leg portion 14 is contoured to fit the calf of a patient wearing the splint. The curved heel portion 16 has an enlarged radius so that the heel portion is typically in spaced relation to the rearward portion of a patient's heel who is wearing the splint.

A toe plate 18 is adjustably secured to the forward end of foot portion 12 by connector 20. The toe plate does not comprise a part of this invention.

Heel portion 16 has a rearward side 22. An elliptical shaped aperture 24 is formed in the rear side 22 of heel portion 16 to permit visual access to the rearward side of a patient's heel who is wearing the splint. Depending on the position of the patient, the rearward side of the heel can be viewed directly through aperture 24, or can be seen by placing a mirror in spaced relation to the aperture so that the rearward portion of the heel can be seen in the mirror.

Figure 3:
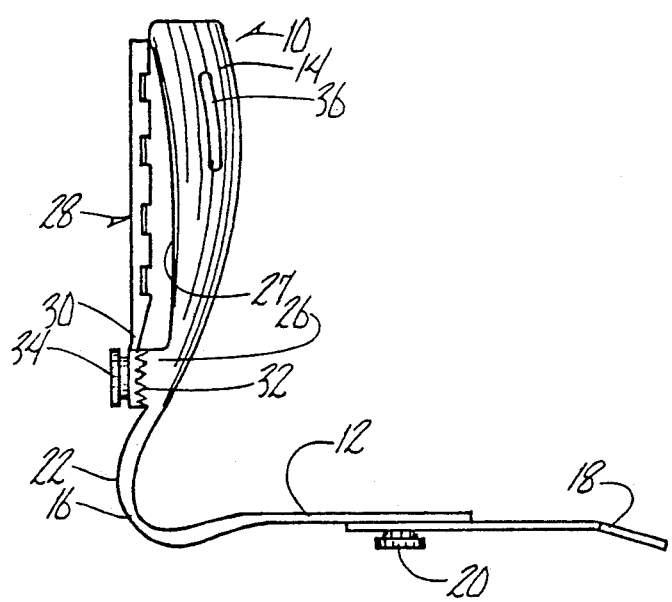
FIG. 3 is a typical side elevational view thereof.
Figure 4:
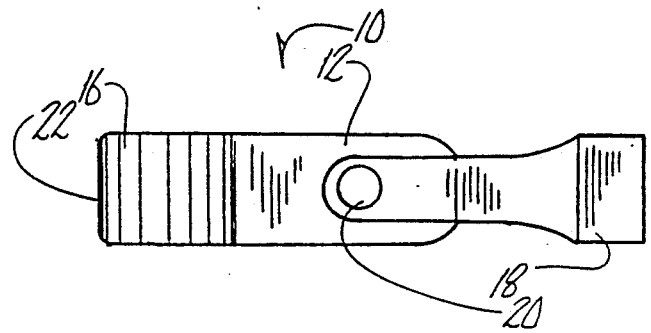
FIG. 4 is a bottom plan view thereof.
Figure 5:
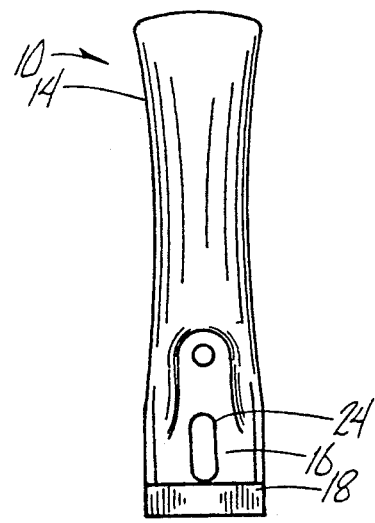
FIG. 5 is a front elevational view thereof.
Figure 6:
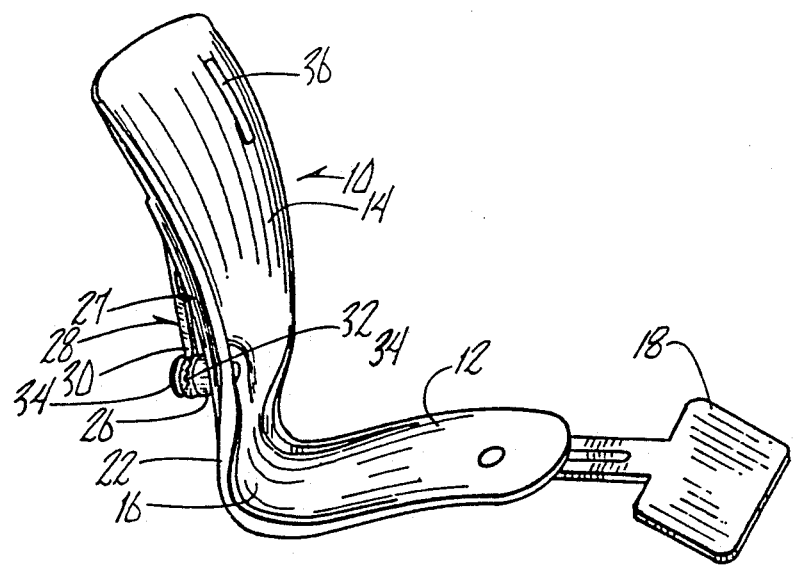
FIG. 6 is a perspective view thereof.

A shoulder 26 extends outwardly from the rear side 27 of leg portion 14 as best shown in FIG. 3. A stabilizer bar 28 is secured by its lower end 30 to shoulder 26 by means of a plurality of ratchet teeth 32 which are formed both in the shoulder 26 and in the lower end of the stabilizer bar. The ratchet teeth 32 on the stabilizer bar and the shoulder are held in any desired position by any conventional connector 34 which typically is a threaded bushing which holds the stabilizer bar 28 in a fixed position when tightened, and which permits stabilizer 28 to be moved to an alternate position when loosened. Typically, the stabilizer bar 28, shown in its inoperative position in FIG. 3, will be rotated in a lateral direction to counteract any tendency of the patient's foot to rotate in an inner or outer direction. The stabilizer bar 28 performs essentially the same function as the stabilizer bar in said U.S. Pat. No. 3,976,059, with the invention herein dwelling in the specific ratchet tooth connection between the stabilizer bar and the leg portion of the splint.

The ratchet teeth 32 make it virtually impossible for the leg or lateral movement of the patient's leg or foot to alter the predetermined position of the stabilizer bar with respect to the splint.

Slots 36 are adapted to receive suitable straps or the like for attaching the splint to the leg of the patient.

Thus, from the foregoing, it is seen that this invention accomplishes at least its stated objectives.

I claim:

1. A plastic foot splint having a horizontal foot portion, a contoured upstanding leg portion, and a heel portion connecting said foot and leg portions, the invention comprising, a stabilizer bar pivotally secured by one if its ends to said leg portion, ratchet teeth located on said one end of said stabilizer bar and on said leg portion at the location of its pivotal connection to said stabilizer bar to permit said stabilizer bar to be selectively held in a fixed position with respect to said leg portion.

2. The foot splint of claim 4 wherein said stabilizer bar is pivotal in a substantially vertical plane with respect to said foot portion.

3. The foot splint of claim 2 wherein said leg portion is contoured to fit the calf of a patient wearing said foot splint and said stabilizer bar is substantially straight.

4. The foot splint of claim 1 wherein a shoulder is formed on said leg portion at the location of its pivotal connection to said stabilizer bar, with the ratchet teeth on said leg portion being formed on said shoulder.

5. The foot splints of claims 2, 3 or 4 wherein said heel portion has a rearward side portion, and an aperture is in said rearward side portion to permit visual examination of the rearward portion of a patient's heel when said foot splint is mounted on one of said patient's feet.

6. A plastic foot splint having a horizontal foot portion, a contoured upstanding leg portion, and a heel portion connecting said foot and leg portions, the invention comprising,
said heel portion having a rearward side portion,
an aperture in said rearward side portion to permit visual examination of the rearward portion of a patient's heel when said foot splint is mounted on one of said patient's feet,
a stabilizer bar being pivotally secured by one if its ends to said leg portions, at a position above said aperture,
ratchet teeth being located on said one end of said stabilizer bar and on said leg portion at the location of its pivotal connection to said stabilizer bar to permit said stabilizer bar to be selectively held in a fixed position with respect to said leg portion.

* * * * *